(12) United States Patent
Pujol et al.

(10) Patent No.: US 10,143,819 B2
(45) Date of Patent: Dec. 4, 2018

(54) PASSIVELY HEATED PATIENT CIRCUIT

(75) Inventors: John Raymond Pujol, Murrysville, PA (US); Jeffrey John Schirm, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 969 days.

(21) Appl. No.: 13/701,552

(22) PCT Filed: Apr. 27, 2011

(86) PCT No.: PCT/IB2011/051834
§ 371 (c)(1),
(2), (4) Date: Dec. 3, 2012

(87) PCT Pub. No.: WO2011/151738
PCT Pub. Date: Dec. 8, 2011

(65) Prior Publication Data
US 2013/0081626 A1   Apr. 4, 2013

Related U.S. Application Data

(60) Provisional application No. 61/351,069, filed on Jun. 3, 2010.

(51) Int. Cl.
*A61M 16/08* (2006.01)
*A61M 16/10* (2006.01)
(Continued)

(52) U.S. Cl.
CPC .... *A61M 16/0875* (2013.01); *A61M 16/0069* (2014.02); *A61M 16/1075* (2013.01); *A61M 16/1095* (2014.02); *A61M 16/0066* (2013.01); *A61M 2016/0039* (2013.01); *A61M 2205/364* (2013.01); *A61M 2205/502* (2013.01);
(Continued)

(58) Field of Classification Search
CPC ...... A61M 2016/0039; A61M 16/0066; A61M 16/0875; A61M 16/1075; A61M 16/1095; A61M 2205/364; A61M 2205/502; F24J 1/00; F28D 20/02; F28D 2021/005; F28F 2255/02
See application file for complete search history.

(56) References Cited

U.S. PATENT DOCUMENTS 4,597,917 A * 7/1986 Lunsford ............ 261/153
4,662,352 A   5/1987 Aviles, Jr.
(Continued)

FOREIGN PATENT DOCUMENTS

CN   201139843 Y   10/2008
CN   101541367 A   9/2009
(Continued)

*Primary Examiner* — Gregory Anderson
*Assistant Examiner* — Elliot S Ruddie
(74) *Attorney, Agent, or Firm* — Michael W. Haas (57) ABSTRACT

Passive heating may be provided to a flexible tube (202) configured to deliver respiratory gas to a patient. A flexible sheathing body (206, 208, 210) may be removably attached to the flexible tube so as to surround the flexible tube and extend along the flexible tube. A passive heating element (218, 220, 222) integrated with the flexible sheathing body may store non-electrical energy and release the stored non-electrical energy as thermal energy to heat the flexible tube.

12 Claims, 3 Drawing Sheets

(51) Int. Cl.
*A61M 16/00* (2006.01)
*F28D 20/02* (2006.01)
*F28D 21/00* (2006.01)
*F24V 30/00* (2018.01)

(52) U.S. Cl.
CPC .............. *F24V 30/00* (2018.05); *F28D 20/02* (2013.01); *F28D 2021/005* (2013.01); *F28F 2255/02* (2013.01)

(56) References Cited

U.S. PATENT DOCUMENTS

| | | | | |
|---|---|---|---|---|
| 4,934,336 | A | * | 6/1990 | White .................... 126/263.01 |
| 5,042,455 | A | * | 8/1991 | Yue et al. ............... 126/263.02 |
| 5,295,964 | A | * | 3/1994 | Gauthier ...................... 604/113 |
| 5,357,948 | A | * | 10/1994 | Eilentropp ............ A61M 16/08 128/203.26 |
| 5,623,922 | A | | 4/1997 | Smith |
| 5,685,296 | A | | 11/1997 | Zdrojkowski |
| 5,937,855 | A | | 8/1999 | Zdrojkowski |
| 7,086,422 | B2 | * | 8/2006 | Huber et al. ................... 138/149 |
| 7,094,219 | B2 | * | 8/2006 | Noice et al. ................... 604/113 |
| 7,537,563 | B2 | * | 5/2009 | Temple ........................ 600/169 |
| 8,078,040 | B2 | * | 12/2011 | Forrester ........... A61M 16/0875 392/481 |
| 2001/0042546 | A1 | | 11/2001 | Umeda |
| 2003/0124277 | A1 | * | 7/2003 | Agarwal .................... A61F 7/02 428/35.2 |
| 2003/0141293 | A1 | | 7/2003 | Takeuchi |
| 2003/0163087 | A1 | * | 8/2003 | Noice et al. ................. 604/113 |
| 2004/0065335 | A1 | | 4/2004 | Huber |
| 2011/0082416 | A1 | * | 4/2011 | Iranitalab ............ A61M 13/003 604/26 |

FOREIGN PATENT DOCUMENTS

| | | |
|---|---|---|
| EP | 1743672 A1 | 1/2007 |
| WO | WO0236051 A1 | 5/2002 |
| WO | WO2008055307 A1 | 5/2008 |

* cited by examiner

FIG. 1

FIG. 3

PASSIVELY HEATED PATIENT CIRCUIT

CROSS-REFERENCE TO RELATED APPLICATIONS

This patent application claims the priority benefit under 35 U.S.C. § 371 of international patent application no. PCT/IB2011/051834, filed Apr. 27, 2011, which claims the priority benefit under 35 U.S.C. § 119(e) of U.S. Provisional Application No. 61/351,069 filed on Jun. 3, 2010, the contents of which are herein incorporated by reference.

BACKGROUND OF THE INVENTION

1. Field of the Disclosure

The invention relates to providing passive heating to a flexible tube configured to deliver respiratory gas to a patient.

2. Description of the Related Art

Various breathing systems use humidifiers to humidify respiratory gases being provided to a patient. For example, positive airway pressure (PAP) machines provide a continuous positive airway pressure to a patient via a suitable user interface (e.g., a respiration mask) for various medical reasons (e.g., treatment of sleep apnea). Humidifiers are frequently provided between or integral with the PAP machine and the user interface in order to humidify the otherwise relatively-dry compressed respiratory gas generated by the PAP machine. Within a heated passover humidifier, water is allowed to evaporate to produce vapor within a reservoir while breathing gas is passed over the surface of the water. Increased water vapor within the reservoir increases the capability to provide more humidity to the respiratory gas that is delivered to a patient. This increase in respiratory gas humidity is accompanied by an increase in the respiratory gas temperature. When the ambient temperature is below the temperature of the respiratory gas being delivered to a patient, condensation can form on the inside of the patient breathing circuit.

Condensation may be reduced by maintaining the temperature of the respiratory gas above the ambient temperature. This may be achieved by insulating and/or heating the patient breathing circuit. Conventionally, heating of the patient breathing circuit is provided via active heating such as resistive heating. In resistive heating, an electric current is passed through a conductor and thermal energy is released due to the electrical resistance of the conductor. Disadvantages of active heating include, for example, the need for an available electrical power source such as a battery pack or an electrical outlet.

One aspect of the invention relates to apparatus for providing passive heating to a flexible tube configured to deliver respiratory gas to a patient. The apparatus may include a flexible sheathing body configured to be removably attached to the flexible tube so as to surround the flexible tube and extend along the flexible tube. The apparatus also may include a passive heating element integrated with the flexible sheathing body. The passive heating element may be configured to store non-electrical energy and to release the stored non-electrical energy as thermal energy to heat the flexible tube.

SUMMARY OF THE INVENTION

Another aspect of the invention relates to a method for providing passive heating to a flexible tube configured to deliver respiratory gas to a patient. The method may include removably attaching a flexible sheathing body to the flexible tube such that the flexible sheathing body surrounds the flexible tube and extends along the flexible tube. The method may also include providing thermal energy to heat the flexible tube from a passive heating element integrated with the flexible sheathing body. The passive heating element may be configured to store non-electrical energy and to release the stored non-electrical energy as thermal energy.

Yet another aspect of the invention relates to apparatus for providing passive heating to a flexible tube configured to deliver respiratory gas to a patient. The apparatus may include sheathing means for surrounding the flexible tube and extending along the flexible tube. The sheathing means may be removably attachable to the flexible tube. The apparatus also may include heating means for storing non-electrical energy and releasing the stored non-electrical energy as thermal energy to heat the flexible tube. The heating means may be integrated with the sheathing means.

Still another aspect of the invention relates to apparatus for respiratory gas delivery. The apparatus may include a flexible tube and a passive heating element. The flexible tube may be configured to deliver respiratory gas to a patient. The passive heating element may be integrated with the flexible tube. The passive heating element may be configured to store non-electrical energy and to release the stored non-electrical energy as thermal energy to heat the flexible tube.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
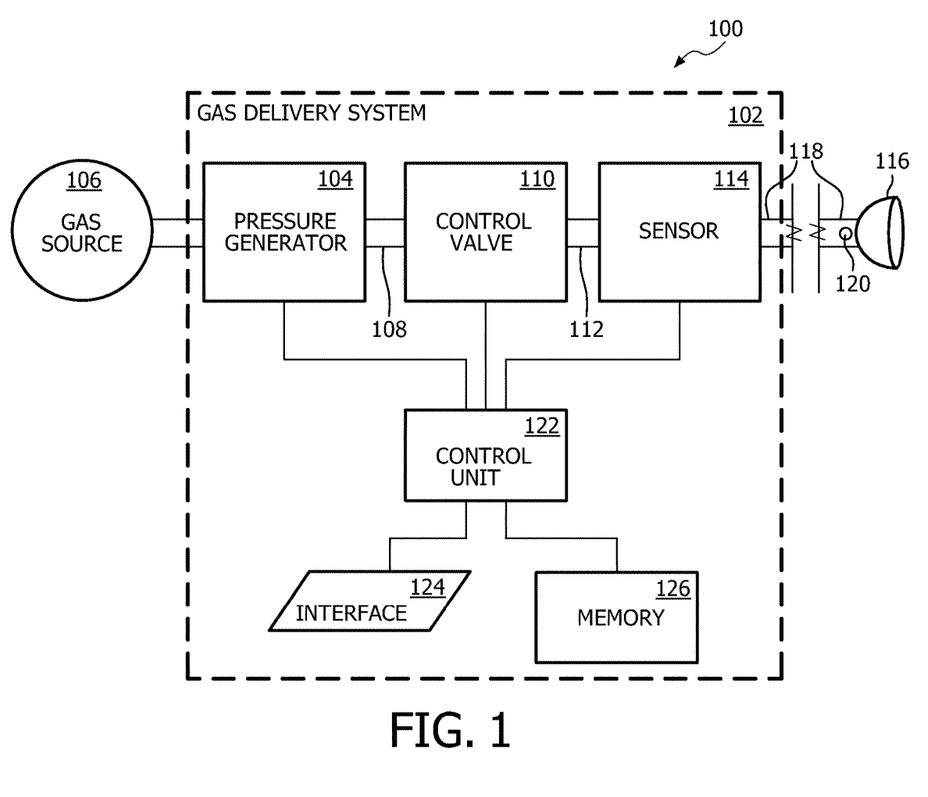
FIG. 1 is a schematic representation of an exemplary patient treatment system.

FIG. 1 schematically illustrates an exemplary patient treatment system 100, in accordance with the present invention. Patient treatment system 100 is capable of providing and automatically controlling the pressure of breathing gas delivered to a patient, while preventing condensation from accumulating in a breathing circuit by passively heating the breathing circuit. Patient treatment system 100 includes a gas delivery system 102 that controls a flow of breathing gas to a patient. Gas delivery system 102 includes a pressure generator 104 that receives a supply of breathing from a breathing gas source 106 and elevates the pressure of that gas for delivery to the airway of a patient. Pressure generator 104 may be any device, such as a blower, piston, or bellows, that is capable of elevating the pressure of the received breathing gas for delivery to a patient. The present invention also contemplates that the pressure generator 104 can be defined by a canister or tank of pressurized gas, with the pressure delivered to the patient being controlled by a pressure regulator. Thus, while the embodiment of FIG. 1 illustrates a separate gas source 106, the gas source may be considered to be part of the gas delivery system 102 in some embodiments.

In addition, in some embodiments, gas source 106 can be provided in the same housing as the rest of gas delivery system 102. In some embodiments, the gas source is not only considered part of the gas delivery system, but also provides the pressurized flow of breathable gas in a manner that can eliminate the separate pressure generator 104. According to some embodiments, the respiratory gas from gas source 106 is delivered with supplemental oxygen from an oxygen source to elevate the level of oxygen concentration in the gas delivered to the patient. This may include mixing the breathable gas from gas source 106 with the supplemental oxygen at gas delivery system 102, or downstream from gas delivery system 102.

According to some embodiments, pressure generator 104 is a blower that is driven at a constant speed during the course of the pressure support treatment to produce a constant pressure or flow rate at its output 108. Driving the blower at a constant speed simplifies the operation of the blower. The present invention contemplates that breathing gas source 106 is any supply of breathing gas, such as ambient atmosphere or a tank of pressurized gas. Furthermore, the breathing gas for delivery to the patient can be any respiratory gas, such as air, oxygen, or an oxygen mixture (e.g., heliox). The breathing gas may also include a mixture of a breathable gas and a medication, which can be in gaseous form (e.g., nitric oxide) or nebulized.

In the illustrated embodiment, the gas delivery system 102 includes a control valve 110. The elevated pressure flow of breathing gas from the pressure generator 104 is delivered to the control valve downstream of pressure generator 104. Control valve 110, either alone or in combination with pressure generator 104, controls the final pressure or flow of gas 112 exiting the pressure/flow generating system, which, in this embodiment includes pressure generator 104 and control valve 110. Examples of a suitable pressure/flow controller include at least one valve, such as sleeve or poppet valve, that exhausts gas from the patient circuit as a method of controlling the pressure in the patient circuit. Other suitable pressure/flow controllers are believed to be well known to those skilled in the art. Some embodiments (not depicted) may not include the control valve 110. In such embodiments, the final pressure exiting the pressure/flow generating system is controlled by the pressure generator 104, as described further herein.

In embodiments in which pressure generator 104 is a blower that operates at all times at only one speed, control valve 110 alone can be used to control the final pressure and flow rate for breathing gas 112 delivered to the patient. In some embodiments, however, the operating speed of pressure generator 104 is controlled in combination with control valve 110 to control the final pressure and flow rate for the breathing gas delivered to the patient. For example, a pressure or flow rate close to the desired pressure or flow rate can be set by establishing an appropriate operating speed for pressure generator 104 along with the control valve 110 so that the two, operating together, determine the final pressure for the breathing gas delivered to the patient. The present invention further contemplates that control valve 110 can be eliminated entirely with the pressure delivered to the patient being controlled by the pressure generator. This embodiment reduces the number of components needed for the pressure treatment system, and hence the cost and complexity.

In the embodiment of FIG. 1, gas delivery system 102 includes a sensor 114. The flow of breathing gas output 112 from control valve 110 is delivered to the sensor 114 to determine one or more parameters associated with the breathing gas output 112. The output of sensor 114 may, for example, determine one or more of the instantaneous volume of gas delivered to the patient, the instantaneous flow rate of gas delivered to the patient, the pressure of gas delivered to the patient, the temperature of gas delivered to the patient, the humidity of gas delivered to the patient, or any other parameter associated with gas delivered to the patient. Sensor 114 is any device suitable for measuring these parameters. In the illustrated embodiment, sensor 114 is provided at a location relatively distant from a patient interface assembly 116. In accordance with some embodiments, however, sensor 114 may be disposed at any location along a patient circuit 118, as will also be described.

The flow of breathing gas is carried from gas delivery system 102 to the patient via patient circuit 118, which is typically a single flexible tube or conduit that carries the flow of breathing gas to a patient interface assembly 116. The patient interface assembly 116 may include a patient interface appliance, which can be either an invasive or a non-invasive, such as a nasal mask, nasal/oral mask, total face mask, nasal cannula, endotracheal tube, tracheal tube, or any other suitable system for communicating a supply of breathing gas to the airway of a patient. Patient interface assembly 116 may also include a headgear assembly (not shown), such as mounting straps or a harness, and/or a proximate portion of patient circuit 118, as will be described later.

Patient interface assembly 116 may also include controls thereon, and other attributes. In the illustrated embodiment, patient interface assembly 116 and/or patient circuit 118 includes a suitable exhaust port 120 for exhausting gas from these components to ambient atmosphere. Exhaust port 120 may be a passive exhaust port in the form of a continuously open port that imposes a flow restriction on the exhaust gas to permit control of the pressure of gas within patient interface assembly 116. It is to be understood, however, that exhaust port 120 can be an active exhaust port that assumes different configurations to control the exhaust rate. Examples of suitable exhaust ports are taught, for example, in U.S. Pat. Nos. 5,685,296 and 5,937,855 both to Zdrojkowski et al.

As shown, gas delivery system 102 includes a controller 122 that controls the various operating aspects of the gas delivery system. For example, the output of sensor 114 is provided to controller 122 for processing, if needed, to determine one or more parameters associated with breathing gas output 112. A control interface 124 provides data and commands to controller 122 of gas delivery system 102. Control interface 124 may include any device suitable to provide information and/or commands to controller 122 via a hardwire or wireless connection. Typical examples of control interface 124 may include a keypad, keyboard, touch pad, mouse, microphone, switches, button, dials, or any other devices that allow a user to input information to patient treatment system 100.

In some embodiments, patient circuit 118 can be a two-limb circuit (not depicted), which is common in conventional invasive ventilators. In a two-limb circuit, the first limb, like patient circuit 118, delivers breathing gas to the patient, except that it lacks an exhaust port. Instead, the second limb carries the exhaust gases from the patient to ambient atmosphere. Typically, an active exhaust port in the second limb under the control of a controller (e.g., the controller 122) provides the desired level of positive end expiratory pressure (PEEP) to the patient. In addition, gas delivery system 102 and related components can include other conventional devices and components, such as a humidifier, heater, bacteria filter, temperature sensor, pressure sensor, flow sensor, humidity sensor, and a gas sensor (e.g., a capnometer), that filter, measure, monitor, and analyze the flow of gas to or from the patient.

Controller 122 controls the actuation of control valve 110 and/or pressure generator 104, thereby controlling the pressure of the breathing gas delivered to the patient. In one embodiment, controller 122 comprises a processor that is suitably programmed with the necessary algorithm or algorithms for calculating gas parameters (e.g., pressure, temperature, humidity, flow, etc.) to be applied to gas delivered to the patient according to various modes of ventilation. In a more advanced embodiment of the present invention, gas delivery system 102 optionally includes a memory 126 associated with controller 122 for storing the programming necessary to perform any of a plurality of modes of ventilation, depending on which mode of ventilation is selected by the caregiver or patient using control interface 124. Memory 126 may also be capable of storing data regarding the operation of patient treatment system 100, input commands, alarm thresholds, as well as any other information pertinent to the operation of the patient treatment system, such as measured values of gas flow, volume, pressure, device usage, operating temperatures, and motor speed.

In embodiments that lack control valve 110 (not depicted), the pressure of breathing gas delivered to the patient is controlled based only on the output of a pressure generator 104. That is, controller 122 controls the pressure of breathing gas delivered to the patient by controlling the motor speed of pressure generator 104. In one embodiment, pressure generator 104 is a blower. According to some embodiments, if necessary, ancillary feedback systems are provided such as a pressure monitor in patient circuit 118, a speed monitor for the blower motor, or a pressure generator output monitor that provides feedback data to controller 122 for controlling the operation of pressure generator 104.

Figures 2A, 2B:
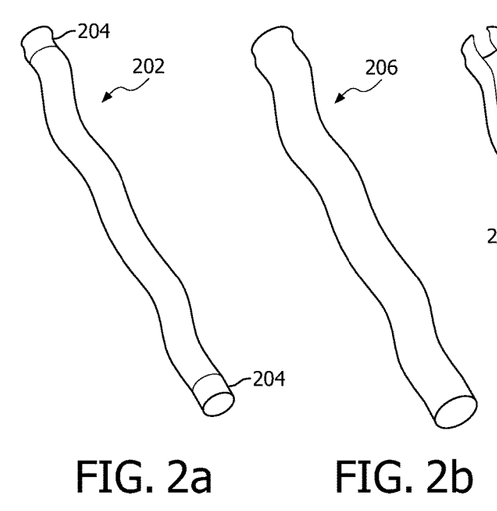
FIG. 2a illustrates exemplary patient breathing circuit tubing.
FIG. 2b illustrates an exemplary passive heating sleeve.

Referring now to FIG. 2a, exemplary patient breathing circuit tubing 202 is illustrated. The patient breathing circuit tubing 202 may be included in a patient circuit, such as the patient circuit 118 depicted in FIG. 1. That is, patient breathing circuit tubing 202 may define all or a portion of patient circuit 118. The patient breathing circuit tubing 202 may include connectors 204, which serve to connect—either permanently or removably—to gas delivery system 102 and/or patient interface assembly 116. The patient breathing circuit tubing 202 is configured to deliver respiratory gas to a patient from, for example, gas delivery system 102. According to various embodiments, the patient breathing circuit tubing 202 may be formed of a flexible material (e.g., plastic), which may be transparent or translucent to permit visual monitoring of patient breathing circuit tubing 202 (e.g., whether condensation is accumulating). Patient breathing circuit tubing 202 may be spirally reinforced in some embodiments.

Heating patient breathing circuit tubing 202 serves to reduce condensation from accumulating within the patient breathing circuit tubing when humidified respiratory gas delivered by the patient breathing circuit tubing has a higher temperature relative to the ambient temperature. Rather than use active heating, the present invention contemplates using passive heating to provide a convenient and effective approach to heating patient breathing circuit tubing 202. Passive heating, as opposed to active heating, does not include resistive heating and, thus, does not require an associated current source (e.g., a battery or power outlet). Passive heating can be provided by a number of mechanisms, at least some of which are discussed further herein.

A variety of apparatus can be implemented to provide passive heating to the patient breathing circuit tubing 202. According to exemplary embodiments, a flexible sheathing body that is configured to be removably attached to the patient breathing circuit tubing 202 may be utilized so as to surround the patient breathing circuit tubing 202. The flexible sheathing body may extend along all or at least a portion of patient breathing circuit tubing 202. Various exemplary form factors of such a flexible sheathing body are described further in connection with FIGS. 2b, 2c, and 2d.

The flexible sheathing body may include a passive heating element integrated with the flexible sheathing body. The passive heating element may be configured to store non-electrical energy and to release the stored non-electrical energy as thermal energy to heat the flexible tube. It is noteworthy that in some embodiments, the passive heating element may be integrated with patient breathing circuit tubing 202 itself such that passive heating is provided to the patient breathing circuit tubing without implementing the flexible sheathing body.

According to exemplary embodiments, the passive heating element may store chemical energy. In some such embodiments, thermal energy may by released by the passive heating element via exothermic oxidation. By way of non-limiting example, the passive heating element may include a combination of cellulose, iron, water as a catalyst, activated carbon to increase reaction speed, vermiculite as a water reservoir, and salt as a catalyst. When the combination is exposed to air, exothermic oxidation may ensue producing heat. Once the exothermic oxidation reaches completion, the combination may not be reused.

The passive heating element may include a super cooled molten material, in accordance with some embodiments. Thermal energy may be released due to exothermic crystallization of the super cooled molten material. By way of non-limiting example, the passive heating element may include sodium acetate trihydrate crystals. Sodium acetate trihydrate crystals melt at approximately 58° C. When heated to approximately 100° C., and subsequently allowed to cool, an aqueous solution containing sodium acetate trihydrate crystals may become supersaturated. Such a solution is capable of super cooling to room temperature without forming crystals. By clicking a metal disc immersed in the solution, a nucleation center is formed that causes the solution to crystallize into solid sodium acetate trihydrate. The bond-forming process of crystallization is exothermic and, thus, releases thermal energy. A passive heating element that includes sodium acetate trihydrate crystals may be "recharged" by boiling the passive heating element until all of the sodium acetate trihydrate crystals are dissolved.

In some embodiments, the passive heating element may include a thermal mass. In such embodiments, the stored non-electrical energy includes stored thermal energy. A thermal mass may be any material having a sufficient thermal capacitance or heat capacity to store, at least temporarily, an appreciable amount of thermal energy. Over time, the thermal energy stored by the thermal mass is released to the surrounding environment. Thermal energy may be introduced to the thermal mass by, for example, submersing the thermal mass in hot water, irradiating the thermal mass using a heat lamp, microwaving the thermal mass, and/or any other method for adding thermal energy to the thermal mass. By way of non-limiting example, the thermal mass may include dried grains (e.g., corn, rice, beans, or buckwheat) that, after being microwaved, release thermal energy over a period of time.

The flexible sheathing body used for surrounding the patient breathing circuit tubing 202 may include an insulating component integrated therewith. The insulating component may be configured to confine, to within the flexible sheathing body, at least a portion of the thermal energy released from the passive heating element. The insulating component may be an insulating layer within the flexible sheathing body or may form at least a portion of the flexible sheathing body.

Figure 2C:
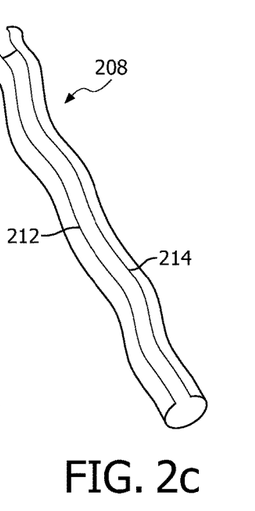
FIG. 2c illustrates an exemplary passive heating cuff.
Figure 2D:
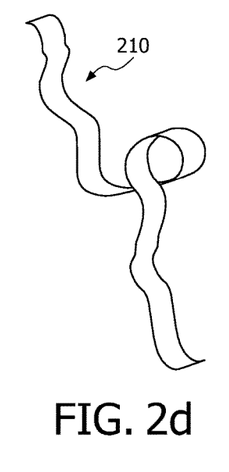
FIG. 2d illustrates exemplary passive heating tape.

The apparatus implemented to provide passive heating to patient breathing circuit tubing 202 may take on a number of form factors, according to various embodiments. FIGS. 2b, 2c, and 2d respectively illustrate an exemplary passive heating sleeve 206, an exemplary passive heating cuff 208, and an exemplary passive heating tape 210, each of which may be implemented as the flexible sheathing body and may include the passive heating element and/or the insulating component. The form factors illustrated in FIGS. 2b, 2c, and 2d are intended to be illustrative and should not be construed as limiting. Any apparatus providing passive heating to a patient circuit is within the scope of the present technology. By way of non-limiting example, a passive heating element may be integrated with patient breathing circuit tubing (e.g., patient breathing circuit tubing 202) such that passive heating is provided to the patient circuit without implementing a flexible sheathing body.

Passive heating sleeve 206 may be configured to slide over the patient breathing circuit tubing 202, thus surrounding patient breathing circuit tubing 202 and extending along the patient breathing circuit tubing. The passive heating element and/or the insulating component may be integrated with passive heating sleeve 206. Passive heating cuff 208 may be configured to enclose the patient breathing circuit tubing 202 by securing together edges 212 and 214 of the passive heating cuff 208. Edges 212 and 214 may have disposed thereon Velcro, snaps, buttons, and/or any other mechanism for removably joining edges 212 and 214. Passive heating tape 210 may be configured to wrap around the patient breathing circuit tubing 202 in a substantially helical manner. Passive heating tape 210 may be secured to patient breathing circuit tubing 202 by way of integrated wire reinforcements, a temporary adhesive, and/or any other mechanism for removably attaching passive heating tape 210 to the patient breathing circuit tubing 202. It is noteworthy that passive heating cuff 208 and passive heating tape 210 may be attached and removed from the patient breathing circuit tubing 202 without disconnecting the patient breathing circuit tubing 202 from the gas delivery system 102 and/or the patient interface assembly 116. Since the flexible sheathing body (e.g., the passive heating sleeve 206, the passive heating cuff 208, and/or the passive heating tape 210) is removably attachable to the patient breathing circuit tubing 202, the flexible sheathing body may be washed, replaced, and/or otherwise serviced separately from the patient breathing circuit tubing 202.

Figure 2E:
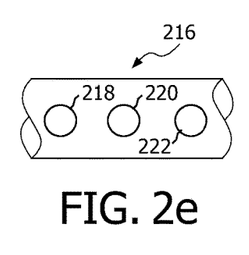
FIG. 2e illustrates a cross-sectional view of a passive heating sleeve, in accordance with an embodiment of the invention.

FIG. 2e illustrates a cross-sectional view 216 of a passive heating sleeve, in accordance with an embodiment of the invention. In cross-sectional view 216, passive heating elements 218, 220, and 222 are discretely located. According to various embodiments, passive heating elements may be distributed at discrete locations along the flexible sheathing body, distributed in a semi-continuous manner along the flexible sheathing body, distributed in a continuous manner along the flexible sheathing body, and/or distributed in any other fashion along the sheathing body.

Figure 3:
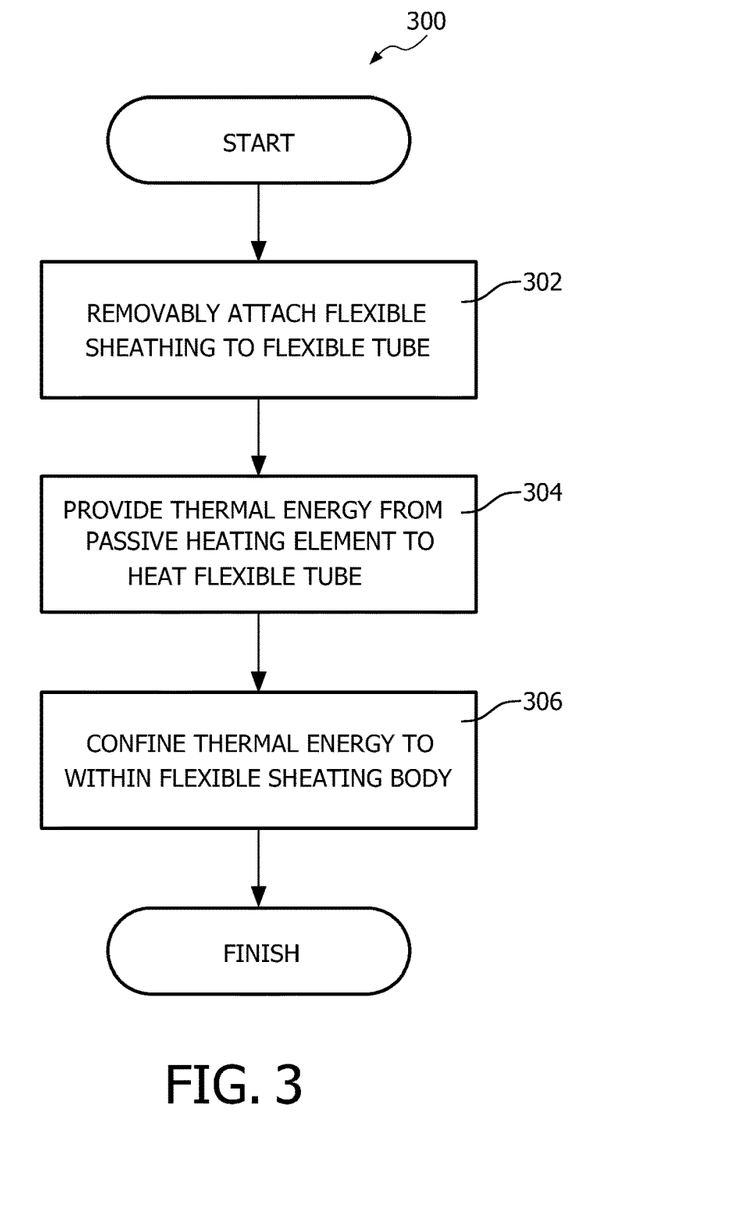
FIG. 3 is a flow chart illustrating an exemplary method for providing passive heating to a flexible tube configured to deliver respiratory gas to a patient.

FIG. 3 is a flow chart illustrating an exemplary method 300 for providing passive heating to a flexible tube (e.g., the patient breathing circuit tubing 202) configured to deliver respiratory gas to a patient. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

At an operation 302, a flexible sheathing body is removably attached to a flexible tube (e.g., the patient breathing circuit tubing 202) such that the flexible sheathing body surrounds the flexible tube and extends along the flexible tube. According to various embodiments, the flexible sheathing body may include the passive heating sleeve 206, the passive heating cuff 208, and/or the passive heating tape 210.

At an operation 304, thermal energy is provided to heat the flexible tube from a passive heating element integrated with the flexible sheathing body. The passive heating element may be configured to store non-electrical energy and to release the stored non-electrical energy as thermal energy. In some embodiments, the thermal energy is provided by way of exothermic oxidation within the passive heating element. The thermal energy may be provided by way of exothermic crystallization within the passive heating element, in accordance with some embodiments. In some embodiments, the thermal energy is provided by way of releasing stored thermal energy.

At an operation 306, at least a portion of the thermal energy released from the passive heating element is confined to within the flexible sheathing body. An insulating component may be implemented to confine thermal energy in some embodiments.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus for providing passive heating to a flexible tube configured to deliver respiratory gas to a patient, the apparatus comprising:
    a passive heating element configured to store non-electrical energy and to release the stored non-electrical energy as thermal energy to heat the flexible tube, the passive heating element comprising:
        (a) a combination of cellulose, iron, water, activated carbon, vermiculite, and salt, wherein the stored non-electrical energy includes chemical energy, and wherein the thermal energy is released due to exothermic oxidization within the passive heating element;
        (b) a super cooled molten material such that the thermal energy is released due to exothermic crystallization of the super cooled molten material, wherein the super cooled molten material includes sodium acetate trihydrate crystals; or
        (c) a thermal mass configured to store and release thermal energy, the thermal mass including dried grains; wherein:
            the passive heating element is disposed in a sheath to form a flat unitary passive heating tape,
            the passive heating tape is configured to be stretched over a surface area of the flexible tube,
            the passive heating tape is wrapped around a portion of a length of the flexible tube in a substantially helical manner to surround the portion of the flexible tube and extend along the portion of the length of the flexible tube, and
            the passive heating tape is removably coupled to the flexible tube by a temporary adhesive.

2. The apparatus of claim 1, wherein the passive heating element comprises the thermal mass including dried grains, the dried grains including one or more of corn, rice, beans, or buckwheat, wherein the thermal mass is configured such that the thermal energy is introduced to the thermal mass via one or more of submersing the thermal mass in hot water, irradiating the thermal mass using a heat lamp, or microwaving the thermal mass.

3. The apparatus of claim 1, further comprising an insulating component integrated with the passive heating tape, the insulating component configured to confine, to within the passive heating tape, at least a portion of the thermal energy released from the passive heating element.

4. The apparatus of claim 1, wherein the flexible tube is connected to a gas delivery system, and wherein the passive heating tape is attached and removed from the flexible tube without disconnecting the flexible tube from the gas delivery system.

5. A method for providing passive heating to a flexible tube configured to deliver respiratory gas to a patient, the method comprising:
    providing a passive heating element configured to store non-electrical energy and to release the stored non-electrical energy as thermal energy to heat the flexible tube;
    disposing the passive heating element in a sheath to form a flat unitary passive heating tape, the passive heating tape being configured to be stretched over a surface area of the flexible tube;
    removably coupling, by a temporary adhesive, the passive heating tape to the flexible tube such that the passive heating tape surrounds the flexible tube and extends along the flexible tube, the passive heating tape being wrapped around the flexible tube in a substantially helical manner along the flexible tube; and
    providing thermal energy to heat the flexible tube from the passive heating element, wherein the thermal energy is provided by:
        (a) exothermic oxidation of a combination of cellulose, iron, water, activated carbon, vermiculite, and salt within the passive heating element,
        (b) exothermic crystallization of sodium acetate trihydrate crystals within the passive heating element, or
        (c) releasing stored thermal energy of a thermal mass comprising dried grains.

6. The method of claim 5, wherein the dried grains include one or more of corn, rice, beans, or buckwheat.

7. The method of claim 5, further comprising confining, to within the passive heating tape, at least a portion of the thermal energy released from the passive heating element.

8. The method of claim 5, wherein the flexible tube is connected to a gas delivery system, and wherein the method further comprises attaching and removing the passive heating tape from the flexible tube without disconnecting the flexible tube from the gas delivery system.

9. An apparatus for providing passive heating to a flexible tube configured to deliver respiratory gas to a patient, the apparatus comprising:
    passive heating means for storing non-electrical energy and releasing the stored non-electrical energy as thermal energy to heat the flexible tube, wherein the thermal energy is provided by way of:
        (a) exothermic oxidation of a combination of cellulose, iron, water, activated carbon, vermiculite, and salt within the passive heating element,
        (b) exothermic crystallization of sodium acetate trihydrate crystals within the passive heating element, or
        (c) releasing stored thermal energy of a thermal mass comprising dried grains, wherein:
            the passive heating means is disposed in a sheath to form a flat unitary passive heating means,
            the passive heating means is configured to be stretched over a surface area of the flexible tube,
            the passive heating means is wrapped around a portion of a length of the flexible tube in a substantially helical manner to surround the portion of the flexible tube and extend along the portion of the length of the flexible tube, and the passive heating means is removably coupled to the flexible tube by temporary adhesive means.

10. The apparatus of claim 9, wherein the thermal energy is provided by the thermal mass comprising dried grains, the dried grains including one or more of corn, rice, beans, or buckwheat, and wherein the thermal mass is configured such that the thermal energy is introduced to the thermal mass via one or more of submersing the thermal mass in hot water, irradiating the thermal mass using a heat lamp, or microwaving the thermal mass.

11. The apparatus of claim 9, further comprising insulating means for confining, to within the passive heating means, at least a portion of the thermal energy released from the heating means, the insulating means being integrated with the passive heating means.

12. The apparatus of claim 9, wherein the flexible tube is connected to a gas delivery system, and wherein passive heating means is attached and removed from the flexible tube without disconnecting the flexible tube from the gas delivery system.

\* \* \* \* \*